US009632333B2

(12) United States Patent
Markus et al.

(10) Patent No.: US 9,632,333 B2
(45) Date of Patent: Apr. 25, 2017

(54) PIEZOELECTRIC SENSOR FOR VISION CORRECTION

(71) Applicants: David T. Markus, Irvine, CA (US); Michael C. Hayes, Irvine, CA (US)

(72) Inventors: David T. Markus, Irvine, CA (US); Michael C. Hayes, Irvine, CA (US)

( * ) Notice: Subject to any disclaimer, the term of this patent is extended or adjusted under 35 U.S.C. 154(b) by 184 days.

(21) Appl. No.: 14/622,814

(22) Filed: Feb. 13, 2015

(65) Prior Publication Data

US 2016/0030160 A1 Feb. 4, 2016

Related U.S. Application Data

(60) Provisional application No. 61/939,736, filed on Feb. 13, 2014.

(51) Int. Cl.
| | |
|---|---|
| *G02C 7/08* | (2006.01) |
| *G02C 7/04* | (2006.01) |
| *A61F 2/16* | (2006.01) |
| *A61B 5/00* | (2006.01) |
| *A61B 5/11* | (2006.01) |

(52) U.S. Cl.
CPC ............... *G02C 7/083* (2013.01); *A61B 5/11* (2013.01); *A61B 5/4851* (2013.01); *A61B 5/6803* (2013.01); *A61B 5/6811* (2013.01); *A61F 2/1624* (2013.01); *G02C 7/049* (2013.01); *G02C 7/081* (2013.01); *A61B 2562/02* (2013.01)

(58) Field of Classification Search
CPC ...... A61B 5/6821; A61B 5/0488; G02C 7/04; G02C 7/083; G02C 7/049; A61F 2/14; A61F 2/141; A61F 2/1613; A61F 2/1624
See application file for complete search history.

(56) References Cited

U.S. PATENT DOCUMENTS

| | | |
|---|---|---|
| 5,914,507 A | 6/1999 | Polla et al. |
| 2011/0228212 A1 | 9/2011 | Blum et al. |
| 2012/0229754 A1 | 9/2012 | Iyer et al. |
| 2013/0194540 A1 | 8/2013 | Pugh et al. |
| 2014/0022505 A1 | 1/2014 | Pugh et al. |
| 2014/0085602 A1 | 3/2014 | Ho et al. |

FOREIGN PATENT DOCUMENTS

JP 2014018234 A * 2/2014

* cited by examiner

*Primary Examiner* — Howie Matthews
(74) *Attorney, Agent, or Firm* — Kafantaris Law Offices; Theo Kafantaris

(57) ABSTRACT

The present invention will provide a vision correction device which utilizes the movements of the eye to correct the focus of the user without the need of surgical procedures. More specifically, the present invention will detect the movement of the ciliary muscle and adaptively modify the shape of an artificial lens positioned inside or outside of the eye to adjust the focus of the lens. This adjustment will occur very rapidly and coincide with the ciliary muscle's attempt to focus the crystalline lens of the eye.

10 Claims, 14 Drawing Sheets

PIEZOELECTRIC SENSOR FOR VISION CORRECTION

CROSS-REFERENCE TO RELATED APPLICATIONS

This application claims the benefit of U.S. Provisional Patent Application No. 61/939,736, filed on Feb. 13, 2014, and incorporated herein by reference.

STATEMENT REGARDING FEDERALLY SPONSORED RESEARCH AND DEVELOPMENT

Not Applicable.

FIELD OF THE INVENTION

This invention relates generally to a piezoelectric sensor for vision correction, and more particularly, to a piezoelectric sensor adapted to detect ciliary muscle movement and shape for vision correction.

DISCUSSION OF RELATED ART

Piezoelectricity can generally be described as an electrical charge in some solid materials, such as crystals, synthetic ceramics, polymers, biological matter such as bone, and organic nanostructures, with the most common material being the ceramic lead zirconate titanate (PZT). When these materials receive mechanical stress or pressure, their stored energy is released as an electrical charge. Common applications for piezoelectricity include ignition devices, fuses, electric cigarette lighters, photovialtic cells, medical equipment, sensors, and transformers.

Piezoelectricity can be used to power small, even nano-sized electronic devices, and can be stored in a capacitor or a battery. A battery will allow for steadier, lower energy output, while a capacitor will allow for higher energy spike during output. The application of piezoelectricity in microprocessors, network circuits, and other nano-sized devices is typically transmitted wirelessly, as it is generally impractical to power nano-sized devices with large-scale energy sources with direct connectivity.

Piezoelectric thin films are very widely used in microelectromechanical systems (MEMS). Here, thin films of piezoelectric material are used as sensors and actuators, where the piezoelectric material deforms in response to an applied electric field. Piezoelectric thin films have also been used in micro motors and micro gears, where the deformation caused by the applied electrical field is converted into linear or rotary motion.

U.S. Pat. No. 5,914,507 to Polla et al. describes a piezoelectric microdevice which uses thin film piezoelectric materials. Specifically, Polla utilizes a deflectable component which is mounted for deflection on a device substrate which has a sensor/actuator. The sensor/actuator has first and second electrodes with a piezoelectric thin film piezoelectric material disposed between the first and second electrodes. The piezoelectric microdevice of Polla are adapted to stress the piezoelectric thin film material when a voltage is applied, resulting in a mechanical deformation or movement through its piezoelectric effect. This force can be transduced to move or position another object, creating a very precise motor.

The human eye, in very simplistic terms, is adapted to provide vision by detecting and converting light into electrical impulses for the brain. The main components of the human eye comprise the pupil, iris, cornea, crystalline lens, zonular fibres, ciliary muscle, retina, and optic nerve. These components work in conjunction to provide a clear and focused image with vibrant colors and proper intensity.

The ciliary muscle is used to adjust the focus of the eye when viewing objects of varying distances. The ciliary muscle, which is circular, is adapted to change the shape of the crystalline lens within the eye, which changes the way light is focused through the lens. When the ciliary muscle contracts, it pulls itself forward, causing the crystalline lens to become more spherical and improving short range focus. Alternatively, when the ciliary muscle relaxes, the crystalline lens is flattened and focal distance is increased. The zonular fibres hold the crystalline lens in its position when not being adjusted by the ciliary muscle.

The human eye is extremely intricate and precise, but the image produced often needs correction. The most common type of vision correction includes glasses and/or contact lenses, which are used to improve vision by correcting refractive error. This is done by directly focusing the light so that it enters the eye with the proper intensity. For those who have trouble focusing their vision, an artificial, intraocular lens can be implanted in the eye to replace a damaged or missing crystalline lens.

While vision correction devices are common in the prior art, there is currently no device which detects specific movements within the eye for focus correction. Furthermore, there is currently no non-surgical means for correcting the focus of the eye without undue burden on the user. Therefore, there is a continued need for a wearable ophthalmic vision correction device which makes use of the movements of the eye to correct the focus of the user without the need of surgical procedures or undue burden. The present invention satisfies these needs.

SUMMARY OF THE INVENTION

The present invention will provide a wearable ophthalmic vision correction device which utilizes the movements of the eye to correct the focus of the user without the need of surgical procedures. More specifically, the present invention will detect the movement of the ciliary muscle and adaptively modify the shape of an artificial lens positioned inside or outside of the eye to adjust the focus of the lens. This adjustment will occur very rapidly and coincide with the ciliary muscle's attempt to focus the crystalline lens of the eye.

More specifically, the present invention comprises a vibration sensor and artificial lens actuator. The vibration sensor comprises a piezoelectric sensor in direct or indirect contact with the eye, with the preferred embodiment in the form of a contact lens. The vibration sensor is adapted to detect the frequencies generated by specific muscle movements within the eye, namely, the ciliary muscle. When these movements are detected, the artificial lens actuator is activated, physically adjusting the shape of a lens for correcting focus. Alternatively, the artificial lens actuator is adapted for use with a display to accommodate the change of focus.

These and other objectives of the present invention will become obvious to those of ordinary skill in the art after reading the following detailed description of the preferred embodiments. It is to be understood that the foregoing general description and the following detailed description

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

The present invention comprises a vibrational sensor 40 in electrical connection with an artificial lens actuator 50 for artificial lens focus correction. When in use, the vibrational sensor 40 is adapted to detect a change of focus within the human eye 20, and once detected, the artificial lens actuator 50 is activated to correct the focus of the user. The vibrational sensor 40 and artificial lens actuator 50 are presented in several embodiments and orientations, each described in further detail below.

Figure 1:
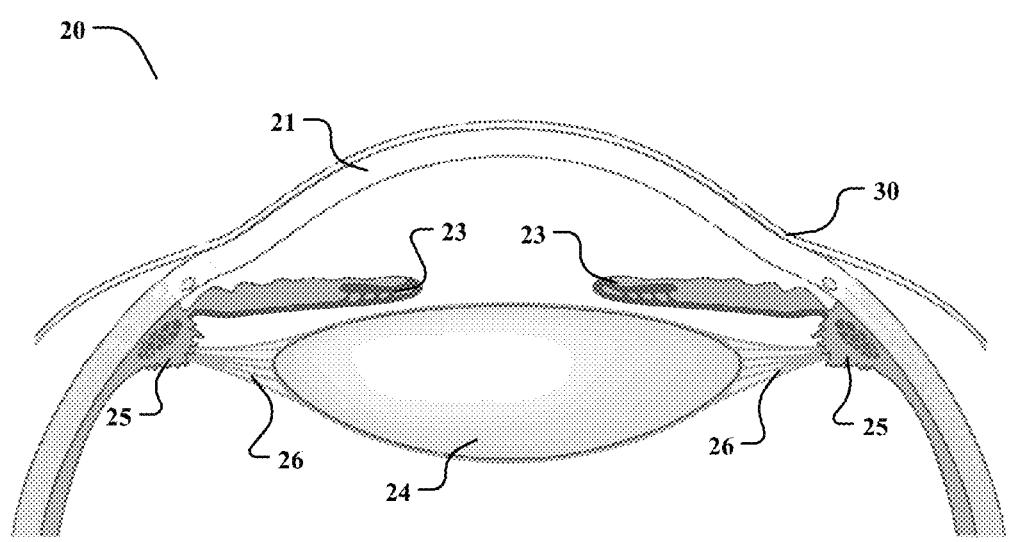
FIG. 1 is a diagram illustrating the relevant anatomy of the eye with contact lens attached.
Figures 2A, 2B:
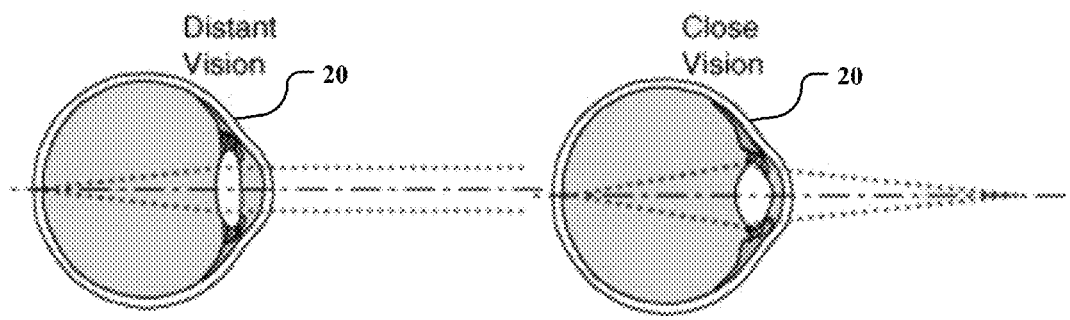
FIG. 2A is a diagram illustrating the change of focus of the eye for distant vision.
FIG. 2B is a diagram illustrating the change of focus of the eye for close vision.
Figure 3:
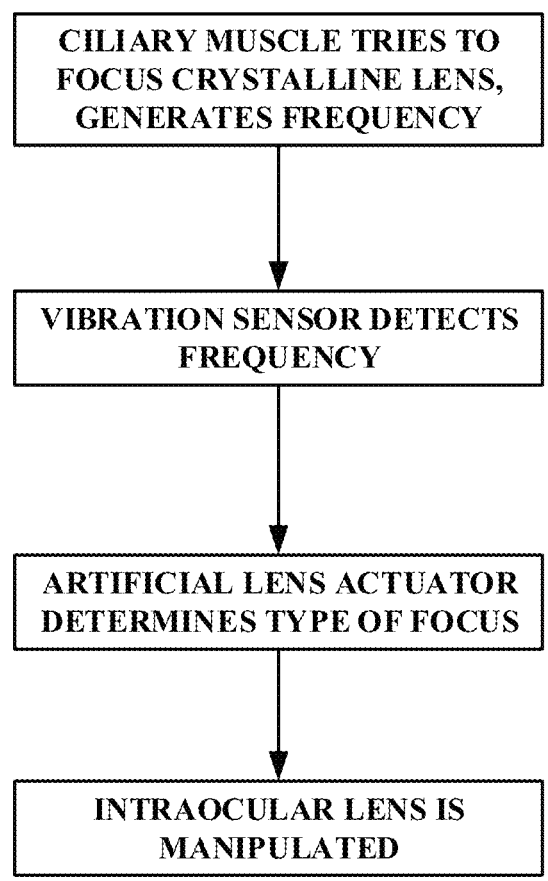
FIG. 3 is a flowchart illustrating the steps of the present invention.

When the ciliary muscles 25 contract, they loosen the ciliary fibers which are attached to the crystalline lens 24. Because the lens 24 is pliable, it relaxes into a more curved shape, increasing its refractive power to accommodate for closer viewing (FIG. 2B). When the eye 20 is relaxed and the crystalline lens 24 is the least rounded, the lens 24 has its maximum focal length for distant viewing (FIG. 2A). As the muscle tension around the ring of the ciliary muscle 25 is increased and the supporting fibers are thereby loosened, the crystalline lens 24 rounds out to its minimum focal length. The iris 23 serves as the aperture stop for the eye 20, closing to about 2 mm in diameter in bright light and opening to a maximum of about 8 mm in dim light.

The vibrational sensor 40 is positioned in close proximity to the eye 20 and is adapted to detect specific activity triggered by a change of focus. More specifically, the vibrational sensor 40 is adapted to detect the movement of the ciliary muscles 25, zonule fibers, suspensory ligaments 26, crystalline lens 24, and iris 23, each of which generates a frequency within a specific range. The vibrational sensor 40 is adapted to monitor and distinguish these frequency from other unwanted frequencies. Furthermore, the vibration sensor 40 is adapted to determine frequency, intensity, force, length, and direction, so as to accurately determine which type and how much focus is desired.

Each individual's ciliary muscles may produce a different frequency and force. Generally, individuals below the age of 50 can produce a maximum force of $1 \times 10^{-2}$N, while those over 50 can produce a maximum force of $0.5 \times 10^{-2}$N. As such, the present invention will further comprise a calibration module for determining the specific frequency and force range for the user. In the preferred embodiment, the frequency range is between 0.01 Hz to 5 Hz and the force sensitivity is between $0.1 \times 10^{-2}$N to $5 \times 10^{-2}$N.

The vibration sensor 40 is a piezoelectric sensor 41 adapted to detect frequencies within this range. The piezoelectric sensor 41 may comprise synthetic piezoelectric ceramics including, but not limited to, barium titanate, lead titanate, lead zirconate titanate, potassium niobate, lithium niobate, lithium tantalite, sodium tungstate, and zinc oxide. Alternatively, the piezoelectric sensor 41 may comprise a polymer piezoelectric such as polyvinylidene fluoride. Lastly, biological piezoelectrics can be used including bone, tendon, silk, wood, enamel, dentin, DNA, and viral protein such as bacteriophage.

The piezoelectric sensor 41 may be implemented in low power and powered embodiments. In the preferred embodiment, the piezoelectric sensor 41 will produce an electrical charge when the piezoelectric material 42 receives the frequencies generated by the movement of the ciliary muscles 25 and/or other muscles within the eye. This non-powered embodiment will save power and lower the complexity of the circuit as it will not require an independent power source. Here, the vibrational sensor 40 is adapted to only respond to a frequency within the above range, although it may generate an electrical charge from all frequencies so as to provide power to other components. In the powered embodiment, an independent power source will provide an electrical charge for the vibrational sensor 40 and other components. More specifically, electrical tunneling of sharp tip shifting is used when there is vibration or a change of capacitance of a structure that moves during the vibration.

Once a frequency is received from the ciliary muscle 25, the vibrational sensor 40 will activate the artificial lens actuator 50, which will artificially adjust the focus for the user. The artificial lens actuator 50 is adapted to physically alter the shape of an artificial lens, or intraocular lens 51, corresponding with the frequency detected by the vibration sensor 40. For example, if the vibration sensor 40 detects that the eye 20 is focusing on an object at a distance, the artificial lens actuator 50 will physically alter the shape of the intraocular lens 51 to focus at a distance. The artificial lens actuator 50, in tandem with the vibration sensor 40, is adapted to determine whether the eye 20 is focusing near or far and at what distance. More specifically, the vibration sensor 40 will relay frequency, intensity, length, and direction information to the artificial lens actuator 50 so as to accurately determine which type and how much focus is desired.

Figure 4:
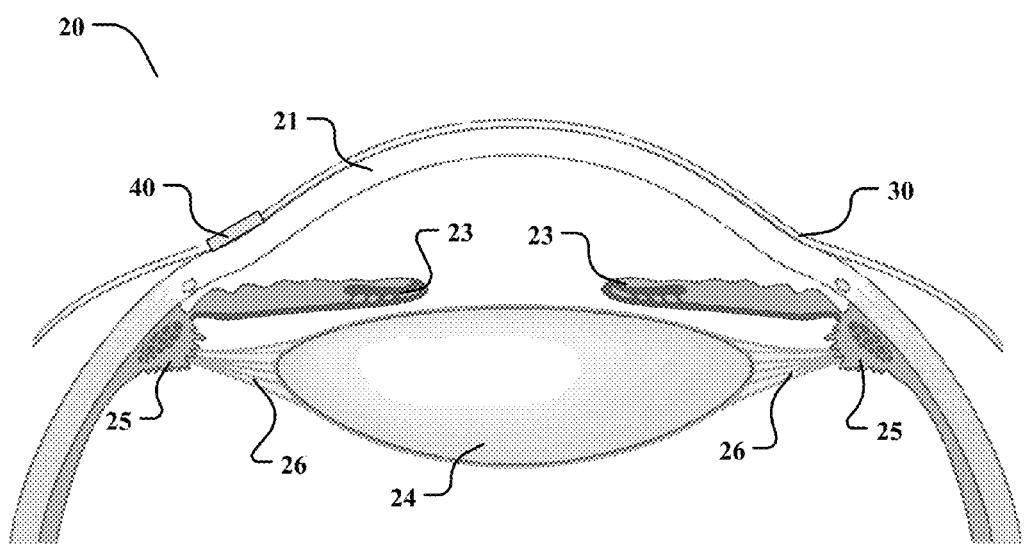
FIG. 4 is a diagram illustrating the first embodiment of the invention.

The present invention may be implemented in several embodiments. In a first embodiment, the vibration sensor 40 is positioned outside of the cornea 21 and will be mechanically coupled with the surface of the cornea 21 for vibration detection (FIG. 4). Here, a contact lens 30 is displayed such that the vibration sensor 40 rests adjacent to the eye 20 when the contact lens 30 is worn. The vibration sensor 40 will activate the artificial lens actuator 50 within the contact lens 30 if a frequency is detected. The contact lens 30 will then adjust the shape of the contact lens 30, adjusting the focus of the eye 20 accordingly. All components must be highly flexible to operate within a stretchable and elastic contact lens 30 and within the delicate structure in and around the eye 20.

Figure 5:
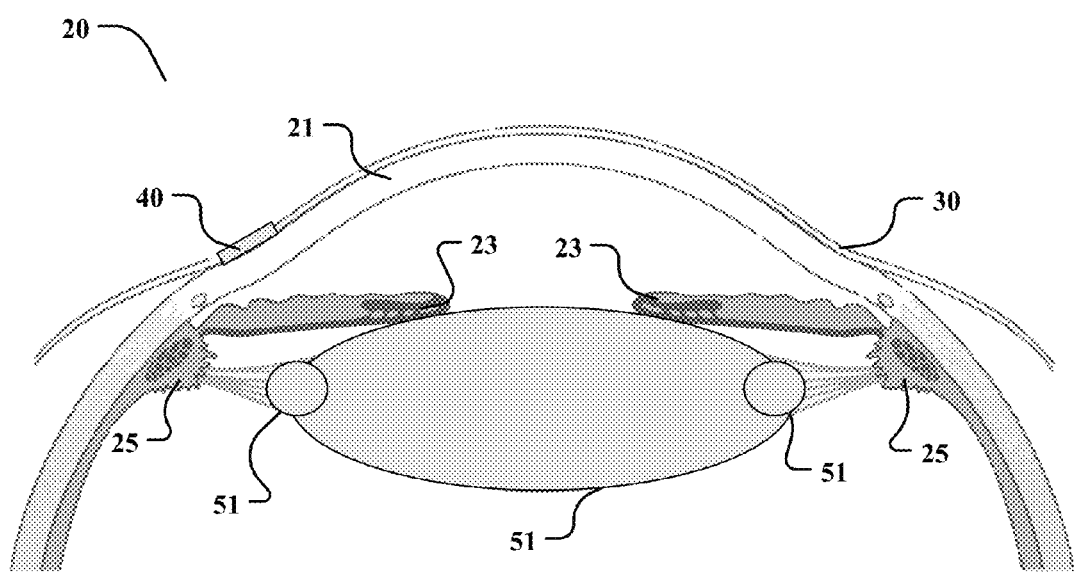
FIG. 5 is a diagram illustrating the second embodiment of the invention.

In a second embodiment, the vibration sensor 40 is positioned within the eye 20 and will be mechanically coupled with the ciliary muscle 40 (FIG. 5). Here, the intraocular lens 51 is positioned such that a pair of vibration sensors 40 are positioned adjacent to the ciliary muscles 25 as they attach to the intraocular lens 51. When a frequency is detected, the artificial lens actuator 50 will change the shape of the intraocular lens 51, thereby adjusting the focus of the eye 20 accordingly.

Figure 6:
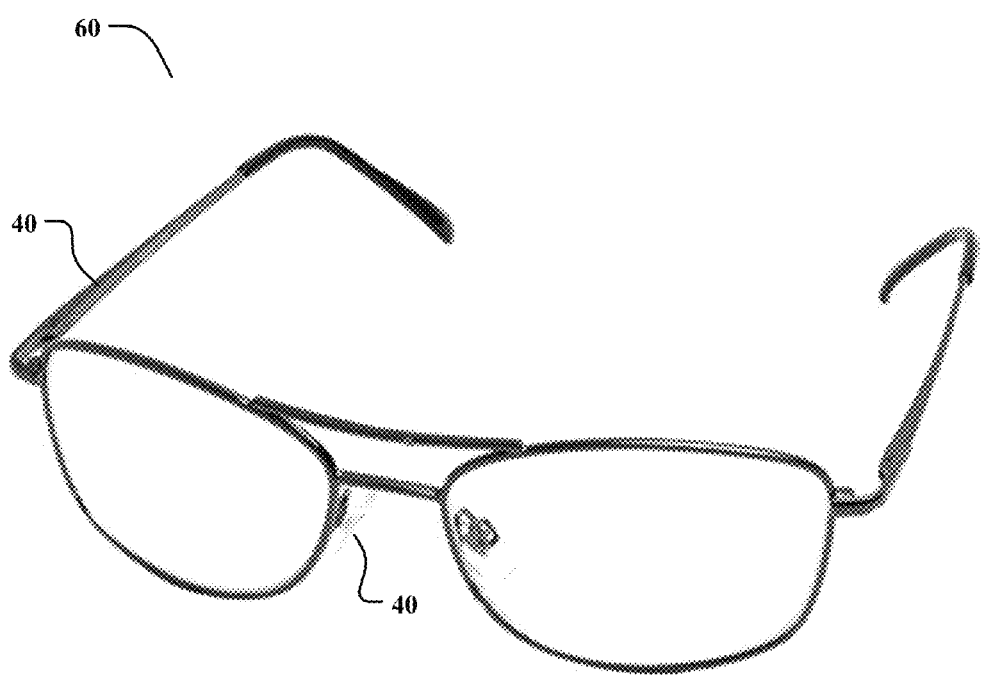
FIG. 6 is a diagram illustrating the third embodiment of the invention.

In a third embodiment, the vibration sensor 40 is positioned outside of the eye 20 on a pair of glasses 60 (FIG. 6). Here, the vibration sensor 40 is positioned on the temples and nose pads of the glasses 60, where there is direct contact with the face of the user. As such, the vibration sensors 40 will be adapted to detect the frequency from the ciliary muscles 25 and/or other movements of the eye 20. Here, if a frequency within the specified range is detected, the artificial lens actuator 50 will adjust the shape of the intraocular lens 51, thereby adjusting the focus of the eye 20 accordingly. Alternatively, the glasses 60 may be adapted to provide a display for the user, and as such, the artificial lens actuator 50 will instead manipulate the display to accommodate the change of focus.

Figure 7:
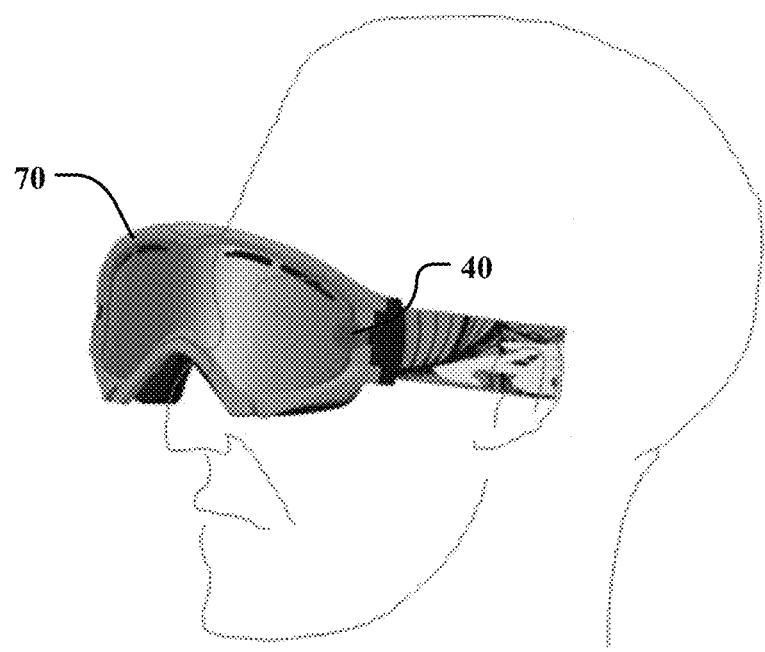
FIG. 7 is a diagram illustrating the fourth embodiment of the invention.

In a fourth embodiment, the vibration sensor 40 is positioned outside of the eye 20 and in wired or wireless communication with goggles 70 or other type of helmet (FIG. 7). Here, the vibration sensor 40 is positioned directly on the user's face in close proximity to the eye 20. The vibration sensor 40 will detect the frequency from the ciliary muscles 25 and/or other movements of the eye 20 and act as a trigger. For example, the goggles 70 or helmet will be adapted to provide a display for the user, and as such, if a frequency is detected, the display 50 may be activated, deactivated, or otherwise trigger a display within the goggles 70 or helmet.

Figure 8:
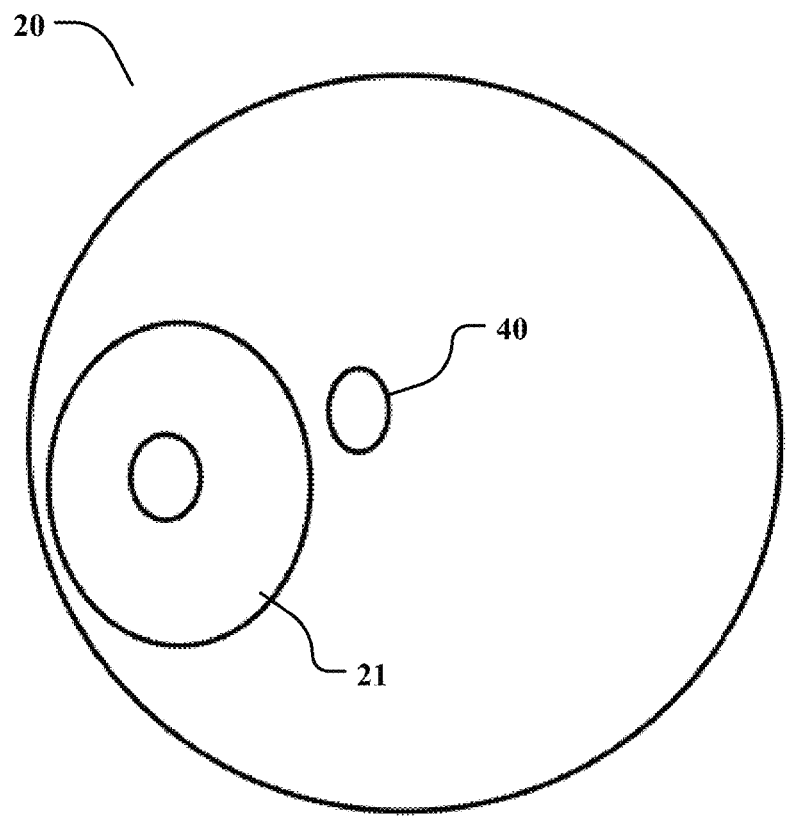
FIG. 8 is a diagram illustrating the fifth embodiment of the invention.

In a fifth embodiment, the vibration sensor 40 is implanted or otherwise directly attached to an artificial or natural eye 20 for vibration detection (FIG. 8). The vibration sensor 40 will detect the frequency from the ciliary muscles 25 and/or other movements of the eye 20 and relay this information to the artificial lens actuator 50 electronically. If the artificial lens actuator 50 is positioned within the eye 20, the communication will be wired, and if outside the eye 20, the communication will be wireless.

Figure 9A:
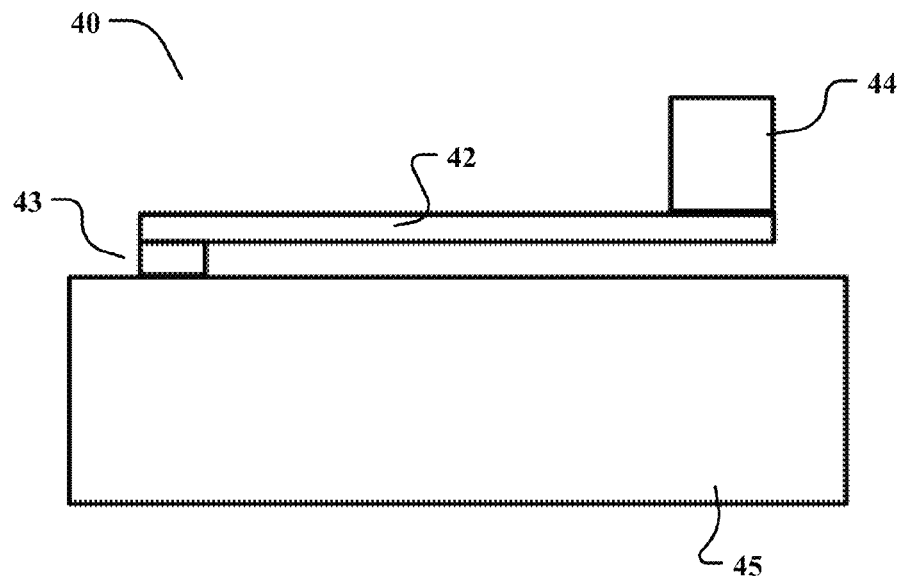
FIG. 9A is a diagram illustrating a cross-sectional view of a first type of vibration sensor.
Figure 9B:
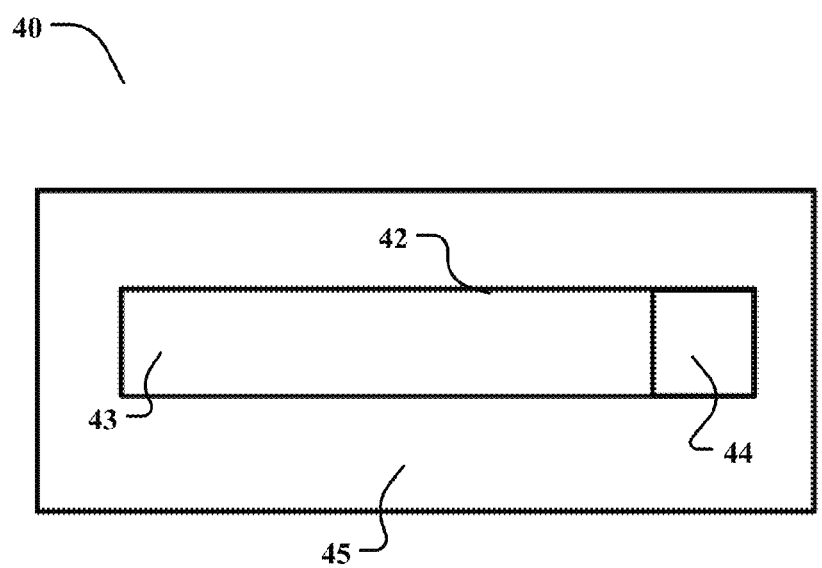
FIG. 9B is a diagram illustrating a top view of a first type of vibration sensor.
Figure 10A:
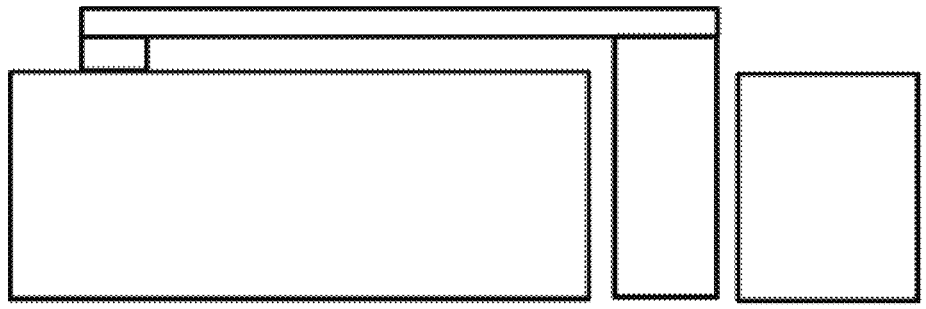
FIG. 10A is a diagram illustrating a cross-sectional view of a second type of vibration sensor.
Figure 10B:
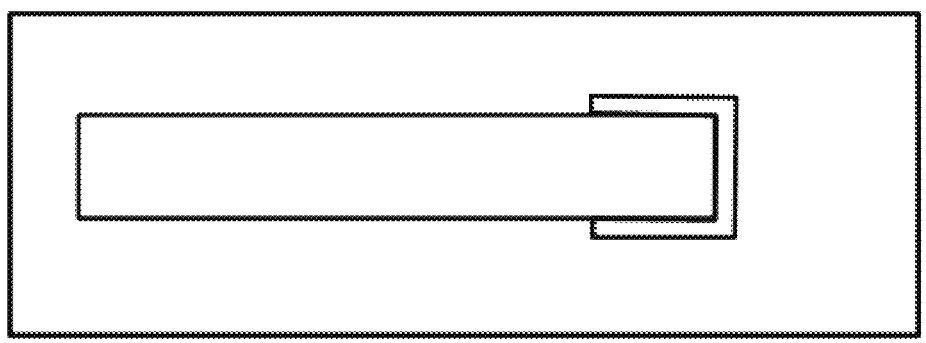
FIG. 10B is a diagram illustrating a top view of a second type of vibration sensor.
Figure 10C:
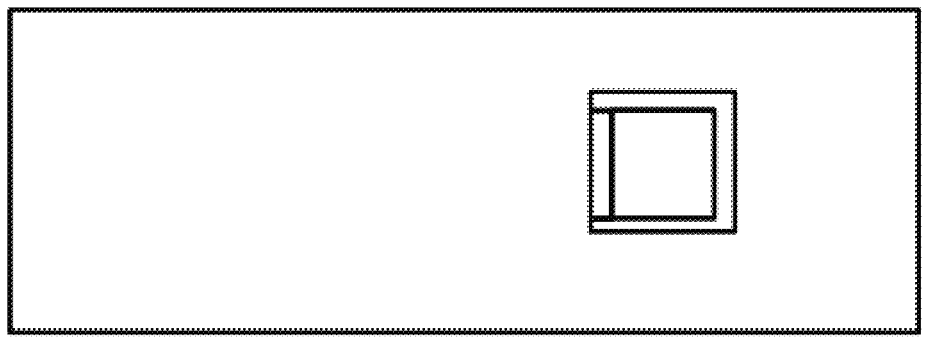
FIG. 10C is a diagram illustrating a bottom view of a second type of vibration sensor.
Figure 11A:
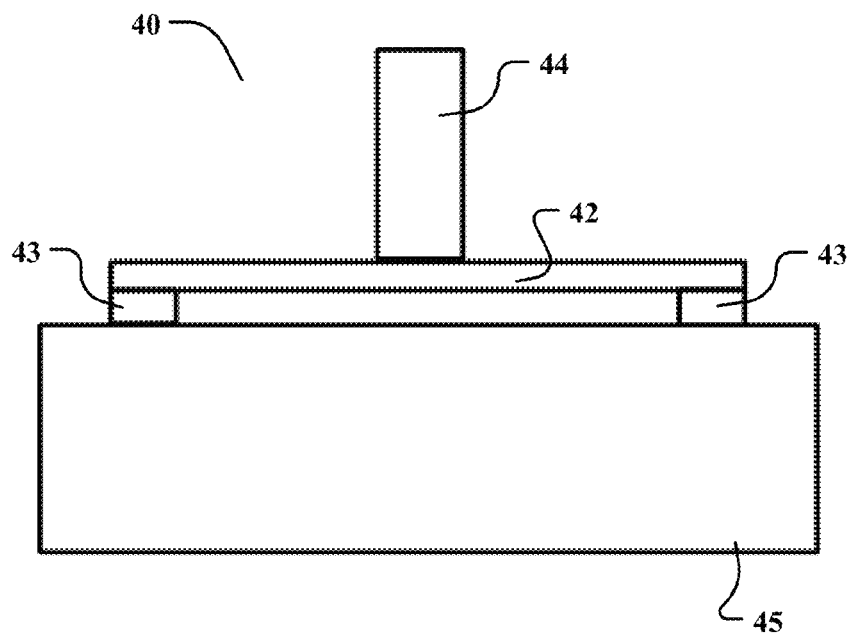
FIG. 11A is a diagram illustrating a cross-sectional view of a third type of vibration sensor.
Figure 11B:
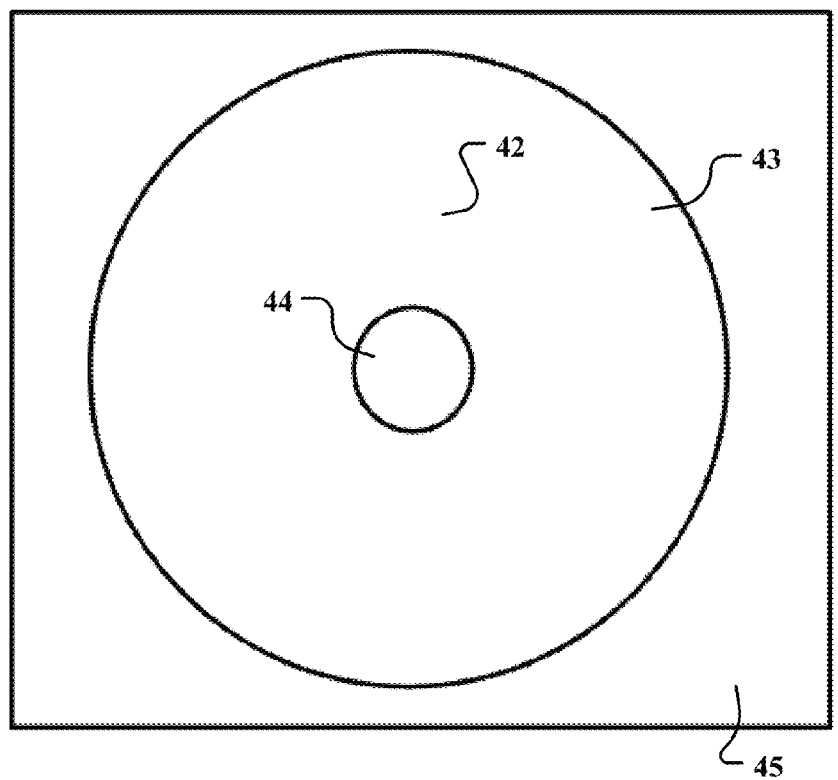
FIG. 11B is a diagram illustrating a top view of a third type of vibration sensor.
Figure 12A:
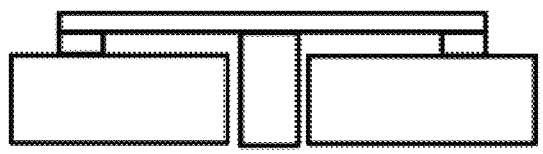
FIG. 12A is a diagram illustrating a cross-sectional view of a fourth type of vibration sensor.
Figure 12B:
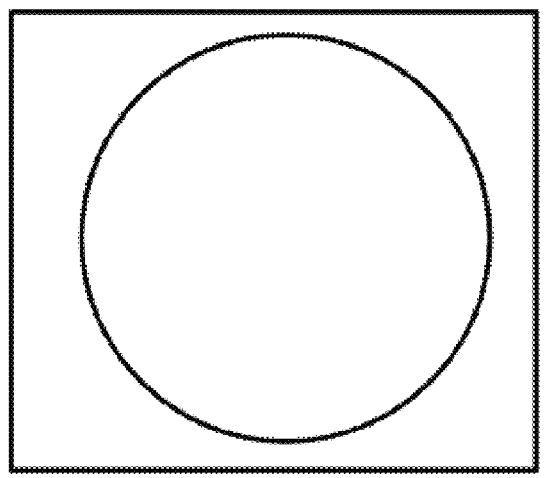
FIG. 12B is a diagram illustrating a top view of a fourth type of vibration sensor.
Figure 12C:
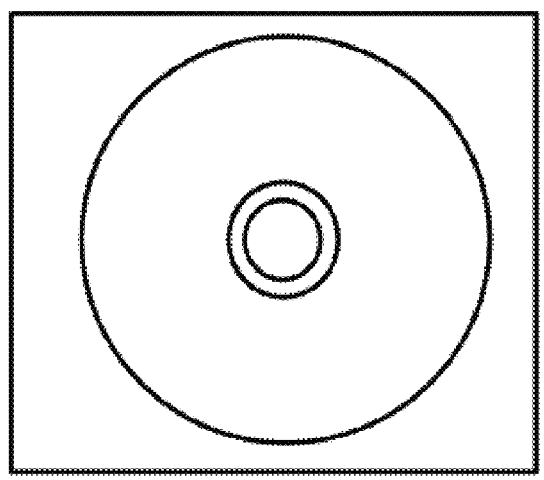
FIG. 12C is a diagram illustrating a bottom view of a fourth type of vibration sensor.
Figure 13:
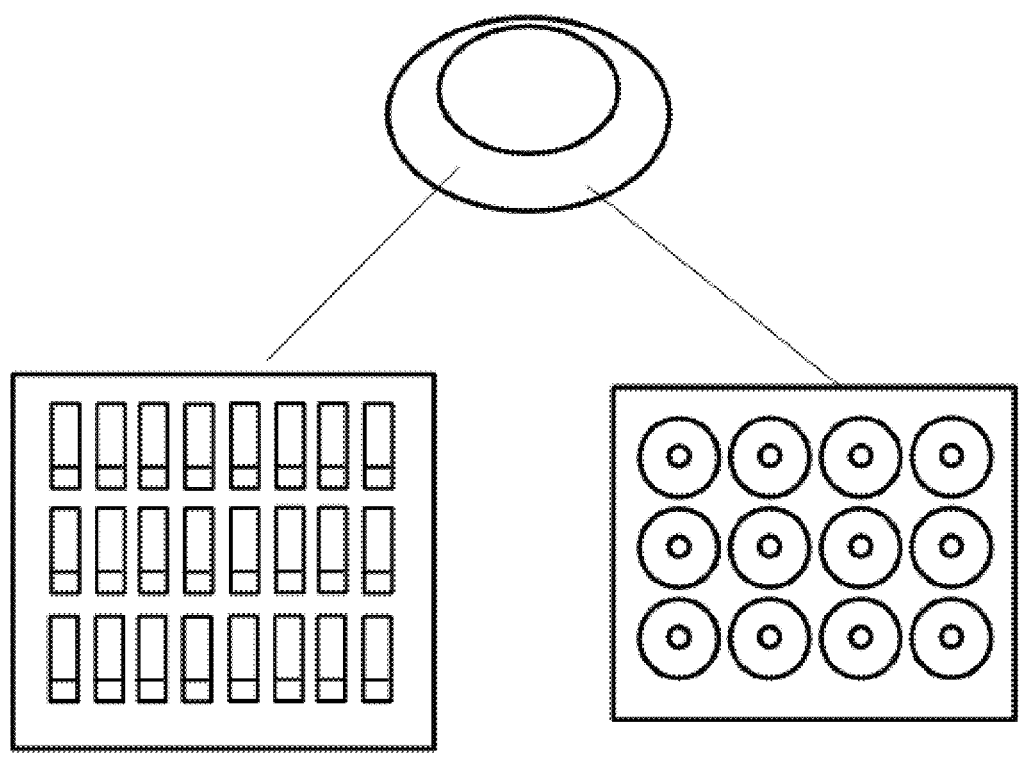
FIG. 13 is a diagram illustrating a piezoelectric sensor array.
Figure 14:
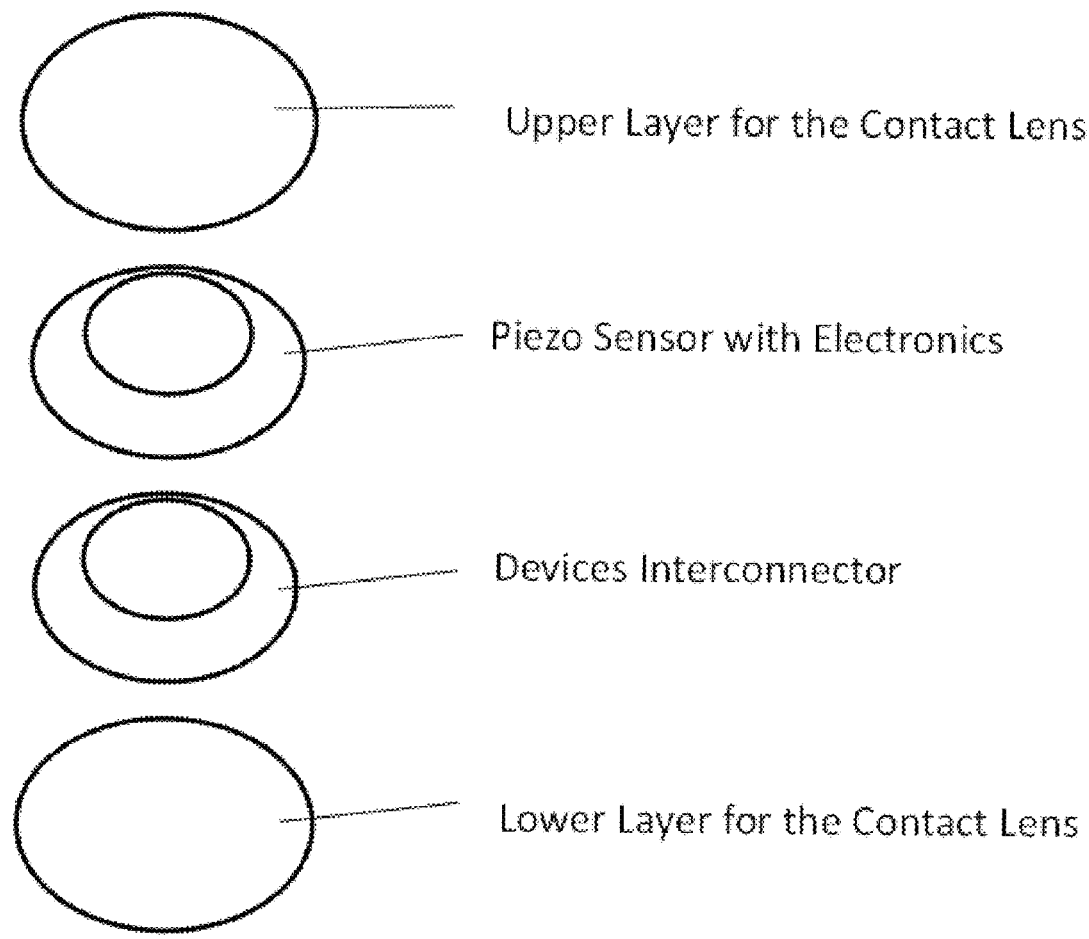
FIG. 14 is a diagram illustrating a contact lens structure of the present invention.

FIGS. 9A and 9B illustrate a type 1 cantilever piezoelectric structure having a clamp 43 on one end. This permits the piezoelectric material 42 to vibrate freely. It has solid interface material at the tip of the cantilever 44 to detect the vibration, while the base 45 is made from silicon. FIGS. 11A and 11B illustrate a type 3 enclosed membrane piezoelectric structure which is clamped 43 on all ends or partially clamped. Here, vibration is detected when the center of the piezoelectric material membrane 42 vibrates with the frequency of the ciliary muscle movements of the eye 20. This embodiment comprises a solid interface material 44 at the tip of the center of the membrane to detect the vibration, while the base 45 is made from silicon. FIG. 13 displays how a piezoelectric sensor array may be positioned on a contact lens. FIG. 14 displays how the layers of the contact lens are positioned.

While the above description contains specific details regarding certain elements, sizes, and other teachings, it is understood that embodiments of the invention or any combination of them may be practiced without these specific details. Specifically, although certain materials and shapes are designated in the above embodiments, any suitable materials or shape may be used. These details should not be construed as limitations on the scope of any embodiment, but merely as exemplifications of the presently preferred embodiments. In other instances, well known structures, elements, and techniques have not been shown to clearly explain the details of the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A system for vision correction comprising:
   a thin film piezoelectric sensor positioned within a contact lens and adapted to detect frequencies corresponding to ciliary muscle movement, wherein said thin film piezoelectric sensor comprises a thin film piezoelectric material positioned between a pair of electrodes having a cantilever structure, wherein one clamp attaches said piezoelectric material and electrodes to a silicon base; and
   an artificial lens actuator in electrical communication with said thin film piezoelectric sensor;
   wherein said thin film piezoelectric sensor will receive and vibrate from frequencies corresponding to distinct muscle movements when the eye attempts to focus, activating said artificial lens actuator for artificial focus correction.

2. The system for vision correction of claim 1, wherein said thin film piezoelectric sensor comprises a bridge structure, wherein two opposing clamps attach said piezoelectric material to said silicon base.

3. The system for vision correction of claim 1, wherein said thin film piezoelectric sensor comprises an enclosed membrane structure, wherein said piezoelectric material is attached to said silicon base on all ends.

4. The system for vision correction of claim 1, wherein said thin film piezoelectric sensor further comprises a piezoelectric material comprising lead zirconate titanate, barium titanate, lead titanate, potassium niobate, lithium niobate, lithium tantalite, sodium tungstate, zinc oxide, polyvinylidene fluoride, bone, tendon, silk, wood, enamel, dentin, DNA, and viral proteins.

5. The system for vision correction of claim 1, wherein said frequencies are between 0.01 Hz to 5 Hz and having a force sensitivity between $0.1 \times 10^{-2}$ N to $5 \times 10^{-2}$ N.

6. The system for vision correction of claim 5, wherein said distinct muscle movements further comprise movement of the ciliary muscles, zonule fibers, suspensory ligaments, crystalline lens, and iris.

7. The system for vision correction of claim 6, wherein said thin film piezoelectric sensor is unpowered, providing an electrical charge to said artificial lens actuator when said distinct muscle movements are detected.

8. The system for vision correction of claim 6, wherein said thin film piezoelectric sensor is powered by an external power source.

9. The system for vision correction of claim 1, wherein said artificial lens actuator is in mechanical communication with said contact lens and is configured to adjust the shape of said contact lens when activated.

10. The system for vision correction of claim 1, wherein said electronic communication is wireless communication.

* * * * *